(12) United States Patent
Poncet et al.

(10) Patent No.: US 9,610,165 B2
(45) Date of Patent: Apr. 4, 2017

(54) HUMERAL COMPONENT OF A SHOULDER JOINT PROSTHESIS

(75) Inventors: Didier Poncet, Bron (FR); Cecile Nerot, Reims (FR); Didier Capon, Sautron (FR); Ludwig Seebauer, Forstinning (DE); Anders Ekelund, Bromma (SE); Lieven De Wilde, Gent (BE); Michael Wirth, San Antonio, TX (US); David Collins, Little Rock, AR (US); Laurent Lafosse, Annecy le Vieux (FR)

(73) Assignees: Cecile Nerot, Raynham, MA (US); Didier Capon, Raynham, MA (US); Ludwig Seebauer, Raynham, MA (US); Anders Ekelund, Raynham, MA (US); Lieven De Wilde, Raynham, MA (US); Laurent Lafosse, Raynham, MA (US); DePuy Synthes Products, Inc., Raynham, MA (US)

( * ) Notice: Subject to any disclaimer, the term of this patent is extended or adjusted under 35 U.S.C. 154(b) by 945 days.

(21) Appl. No.: 12/088,907

(22) PCT Filed: Oct. 2, 2006

(86) PCT No.: PCT/IB2006/002952
§ 371 (c)(1),
(2), (4) Date: Feb. 9, 2009

(87) PCT Pub. No.: WO2007/039820
PCT Pub. Date: Apr. 12, 2007

(65) Prior Publication Data
US 2009/0171462 A1    Jul. 2, 2009

(30) Foreign Application Priority Data
Oct. 1, 2005  (GB) .................................. 0519994.8

(51) Int. Cl.
*A61F 2/40* (2006.01)
*A61F 2/30* (2006.01)

(52) U.S. Cl.
CPC .......... *A61F 2/4059* (2013.01); *A61F 2/4014* (2013.01); *A61F 2002/305* (2013.01);
(Continued)

(58) Field of Classification Search
USPC ............................................ 623/19.11–19.14
See application file for complete search history.

(56) References Cited

U.S. PATENT DOCUMENTS

| 5,314,479 A | 5/1994 | Rockwood, Jr. et al. |
| 5,358,526 A | 10/1994 | Tornier |

(Continued)

FOREIGN PATENT DOCUMENTS

| DE | 19841612 A1 | 3/2000 |
| EP | 0339530 A | 11/1989 |

(Continued)

OTHER PUBLICATIONS

PCT Written Opinion, 7 pages Jan. 8, 2008.
(Continued)

*Primary Examiner* — Marcia Watkins

(57) ABSTRACT

A humeral component of a reverse shoulder prosthesis includes a stem part configured for location within the intramedullary cavity of the humerus, the stem part having a stem axis, an epiphyseal part connected to the elongate stem part and having a concave bearing surface defining an epiphyseal axis, and wherein the epiphyseal axis is offset posteriorly relative to the stem axis.

40 Claims, 6 Drawing Sheets

(52) U.S. Cl.
CPC .............. *A61F 2002/3054* (2013.01); *A61F 2002/3082* (2013.01); *A61F 2002/30253* (2013.01); *A61F 2002/30331* (2013.01); *A61F 2002/30487* (2013.01); *A61F 2002/30507* (2013.01); *A61F 2002/30512* (2013.01); *A61F 2002/30538* (2013.01); *A61F 2002/30604* (2013.01); *A61F 2002/30616* (2013.01); *A61F 2002/30617* (2013.01); *A61F 2002/30884* (2013.01); *A61F 2002/4022* (2013.01); *A61F 2002/4037* (2013.01); *A61F 2002/4044* (2013.01); *A61F 2002/4051* (2013.01); *A61F 2220/0025* (2013.01); *A61F 2220/0033* (2013.01); *A61F 2230/0076* (2013.01); *A61F 2250/0006* (2013.01); *A61F 2250/0097* (2013.01); *A61F 2310/00011* (2013.01)

(56) References Cited

U.S. PATENT DOCUMENTS

| | | | |
|---|---|---|---|
| 5,910,171 A | 6/1999 | Kummer | |
| 6,790,234 B1 | 9/2004 | Frankle et al. | |
| 6,863,690 B2 | 3/2005 | Ball | |
| 7,169,184 B2* | 1/2007 | Dalla Pria | 623/19.12 |
| 7,758,650 B2* | 7/2010 | Dews et al. | 623/19.14 |
| 2001/0054624 A1* | 12/2001 | Jourdin et al. | 222/321.7 |
| 2004/0064187 A1 | 4/2004 | Ball | |
| 2004/0064190 A1 | 4/2004 | Ball | |
| 2004/0143335 A1* | 7/2004 | Dews et al. | 623/19.14 |
| 2004/0220673 A1* | 11/2004 | Pria | 623/19.12 |
| 2004/0220674 A1 | 11/2004 | Pria | |
| 2011/0060417 A1* | 3/2011 | Simmen et al. | 623/19.11 |

FOREIGN PATENT DOCUMENTS

| | | |
|---|---|---|
| EP | 0679375 A1 | 11/1995 |
| EP | 0815810 A1 | 1/1998 |
| EP | 1402854 A | 3/2004 |
| EP | 1472999 A | 11/2004 |
| FR | 2579454 A1 | 10/1986 |
| FR | 2699400 A1 | 6/1994 |
| FR | 2821545 A1 | 9/2002 |
| WO | WO 9725943 A1 | 7/1997 |
| WO | WO 03/005933 A | 1/2003 |
| WO | WO 2006/045949 | 5/2006 |

OTHER PUBLICATIONS

International Search Report, dated May 30, 2007, 10 pages.
UK Search Report, dated Jan. 23, 2006, 3 pages.
Argomedical AG; German Patent No. DE19841612A1; Mar. 16, 2000 English Abstract; Derwent World Patents Index; © 2010 Derwent Information Ltd. Dialog® File No. 351 Accession No. 10388629.
S + G Implants GMBH, European Patent No. EP0339530A2; Nov. 2, 1989 English Abstract; MicroPatent Report; 2010 MicroPatent LLC.
EUROS Société Anonyme ; European Patent No. EP0679375A1, Nov. 2, 1995; English Abstract; MicroPatent Report; 2010 MicroPatent LLC.
Tornier SA; European Patent No. EP0815810A1, Jan. 7, 1998; English Abstract; Derwent World Patents Index; © 2010 Derwent Information Ltd. Dialog® File No. 351 Accession No. 9059091.
Rambert Andre; French Patent No. FR 2579454A1, Oct. 3, 1986; English Abstract; Derwent World Patents Index; © 2010 Derwent Information Ltd. Dialog® File No. 351 Accession No. 3843947.
Medinov (S.A.); French Patent No. FR2699400A1, Jun. 24, 1994; English Abstract; Derwent World Patents Index; © 2010 Derwent Information Ltd. Dialog® File No. 351 Accession No. 6838357.
Aston Medical Limited, French Patent No. FR2821545A1, Sep. 6, 2002; English Abstract; Derwent World Patents Index; © 2010 Derwent Information Ltd. Dialog® File No. 351 Accession No. 12783035.
U.S. Appl. No. 11/577,966, filed Oct. 25, 2005; Office Action dated Apr. 30, 2010.
DUOCENTRIC®, Product Information Literature, Aston-Medical — Saint Etienne, France — to the best of our knowledge, 2007.

* cited by examiner

HUMERAL COMPONENT OF A SHOULDER JOINT PROSTHESIS

CROSS REFERENCE TO RELATED APPLICATION

The present application is a continuation of International Patent Application PCT/IB2006/002952 filed Oct. 2, 2006.

BACKGROUND OF THE INVENTION

This invention relates to a humeral component of a reverse shoulder joint prosthesis.

BRIEF SUMMARY OF THE INVENTION

A shoulder joint prosthesis comprises a humeral component having a stem part which can be fitted into the intramedullary cavity of the humerus, and a glenoid part. In the natural joint, the humeral component provides a convex head, which articulates against a concave bearing surface on the glenoid. This structure is reproduced in so-called "anatomic" shoulder joint prostheses, in which the humeral component includes a stem part, and a head part with a convex bearing surface and the glenoid component provides a concave bearing surface. The stem part is implanted within the humerus. The head part is fitted to the stem part (generally using a spigot and socket arrangement) so that it sits above the resection plane of the humerus. Anatomic prostheses are suitable for implantation in patients in which joint tissue has degraded (for example due to arthritis).

The use of modular components to form the humeral component of a shoulder joint prosthesis is known, particular in relation to anatomic shoulder joint prostheses. For example, such modular components are disclosed in U.S. Pat. No. 5,314,479 and U.S. Pat. No. 5,358,526. The connection between stem and head parts of anatomic shoulder joint prostheses can provide for a variable offset between the two parts, to suit the anatomy of a particular patient.

The structure of the anatomic joint is reverse in so-called "reverse" shoulder joint prostheses, in which the glenoid component includes a convex head, and the humeral component has a concave recess in the epiphysis, in which the head on the glenoid component can be received and articulate. In contrast with anatomic shoulder joint prostheses, the humeral component of the reverse joint prosthesis, including the epiphyseal part which provides the bearing surface, is implanted almost entirely within the humerus.

The biomechanical properties of the patient's joint are altered when a reverse shoulder joint prosthesis is implanted because the prosthesis results in the centre of rotation of the joint being shifted medially. A reverse shoulder joint prosthesis is suitable for implantation in a patient with damaged cuff muscle tissue. The shift of the centre of rotation then allows manipulation of the arm using the deltoid muscle because of the increased mechanical advantage that results.

There are significant differences between anatomic and reverse shoulder joint prostheses in terms of design features and techniques for implantation. In an anatomic shoulder joint prosthesis, the angle between the axis of the humeral head (which is the axis of symmetry of the head, usually passing through the pole of the sphere of which the bearing surface of the head forms a part) and the stem axis is about 135°. In a reverse shoulder joint prosthesis, the corresponding angle is generally larger, for example about 155°. Further-more, in a reverse shoulder joint prosthesis, it is known to introduce an anteversion angular offset between the epiphysis and the stem part of up to about 40°, for example of about 20°. This angular offset can improve the range of movement of the joint after implantation, in particular increase the range of internal rotation. This can be achieved in a humeral component which comprises modular stem and epiphyseal parts by rotating the epiphyseal part relative to the stem part about the stem axis.

According to the present invention, it has been found that the range of joint articulation can be increased further in a reverse shoulder joint prosthesis by offsetting the epiphyseal axis of the humeral component posteriorly relative to the stem axis.

Accordingly, in one aspect, the invention provides a humeral component of a reverse shoulder prosthesis, which comprises an elongate stem part for location within the intramedullary cavity of the humerus, and an epiphyseal part having a concave bearing surface for articulation with the convex bearing surface of a glenoid component, in which the elongate stem part defines a stem axis and the concave bearing surface of the epiphyseal part defines an epiphyseal axis, and in which the epiphyseal axis is offset posteriorly relative to the stem axis.

The humeral component of the invention has the advantage of allowing increased range of joint articulation (in particular, internal rotation). This is achieved by creating a lever arm for the subscapularis (which contributes to defining the range of internal rotation).

A further significant advantage of the humeral component of the invention is that the risk of impingement between the rim of the epiphyseal part and cortical tissue of the humerus is reduced, in particular when there is an anteversion angular offset between the stem and epiphyseal parts. Such impingement can be a significant disadvantage because it can require removal of cortical bone tissue to enable the humeral component to be implanted. This can give rise to undesirable weakening of the patient's tissue. This is a problem that is particular to reverse shoulder joint prostheses because of the location of the epiphyseal part of the humeral component within the humerus.

Reducing or avoiding impingement between the epiphyseal part of the humeral component and cortical tissue can allow a larger epiphyseal part to be implanted which can provide advantages in terms of load transfer. It can provide a better fit of the humeral component in the patient's humerus and can allow the component to be fixed more securely.

Preferably, the distance between the stem axis and the epiphyseal axis is at least about 1.0 mm, more preferably at least about 1.5 mm, for example at least about 2.0 mm. Preferably, the distance between the stem axis and the epiphyseal axis is not more than about 7 mm, more preferably not more than about 5 mm, for example not more than about 3.0 mm.

Generally, the stem part and the epiphyseal part will be provided as separate parts, each having a connection feature which allows the parts to be assembled for use. For example, the connection feature on one of the stem part and the epiphyseal part can be a socket and the connection feature on the other of the stem part will then be a spigot which can be received in the socket. Preferably, the spigot and socket are circular in cross-section and are have matching tapers so that they can lock together when pressed together. As is known, a suitable taper angle can be between 6 and 8°.

It can be preferred for the posterior offset of the epiphyseal axis relative to the stem axis can arise as a result of the connection feature (for example a socket which is tapered inwardly towards its closed end) on the epiphyseal part being offset relative to the epiphyseal axis.

Preferably, the epiphyseal part of the humeral component comprises a shell part which defines a recess, and a bearing part which can be received in the shell part and which provides the bearing surface for articulation with a glenoid component. The shell part and the bearing part can be made from different materials. In particular, the bearing part can be made from a material which provides for low friction articulation with the convex bearing surface of the glenoid component. Suitable polymeric materials include ultrahigh molecular weight polyethylene. Ceramic and metallic materials can also provide the bearing surface of the humeral component.

The stem part and at least part of the epiphyseal part of the humeral component will generally be made from metallic materials. Suitable metallic materials for use in orthopaedic joint prostheses are known, and include cobalt-chromium-molybdenum alloys, certain stainless steels, titanium and certain of its alloys.

Preferably, the rim of the shell part is approximately circular. Preferably, the rim of the shell part is approximately planar. When implanted, the plane defined by the rim of the shell part will be arranged approximately parallel to the humeral resection plane, with the distance between the two planes being preferably at least about 1.0 mm, and preferably not more than about 4.0 mm, more preferably not more than about 2.5 mm.

Preferably, when the rim of the shell part is planar, the plane defined by the rim of the shell part is approximately perpendicular to the epiphyseal axis. However, in embodiments in which the rim is non-planar (for example because of a localised lip which is provided to reduce the risk of dislocation), the axis is considered to pass through the pole of the sphere of which the bearing surface forms a part, arranged symmetrically around the pole (apart from the localised lip or similar feature).

Preferably, the angle between the stem axis and the epiphyseal axis, when viewed along the anterior-posterior axis, is at least about 20°. Preferably, the said angle is not more than about 35°, for example about 25°.

The humeral component of the invention can be used with a glenoid component of a reverse shoulder joint prosthesis having features which are known from existing joint prostheses, for example from that sold by DePuy Products Inc under the trade mark DELTA. Such glenoid components include a metaglene component which is fastened to the glenoid by means of fixation screws. A glenosphere component is then mounted on the metaglene component, and fastened to it by means of an inter-engaging spigot and socket arrangement.

In another aspect, the invention provides a shoulder joint prosthesis which comprises a humeral component as discussed above, and a glenoid component which includes a convex head part which can be received in the epiphyseal part of the humeral component and articulate with its concave bearing surface.

BRIEF DESCRIPTION OF THE DRAWINGS

Embodiments of the invention will now be described by way of example with reference to the accompanying drawings, in which.

DETAILED DESCRIPTION OF THE INVENTION

Figure 1:
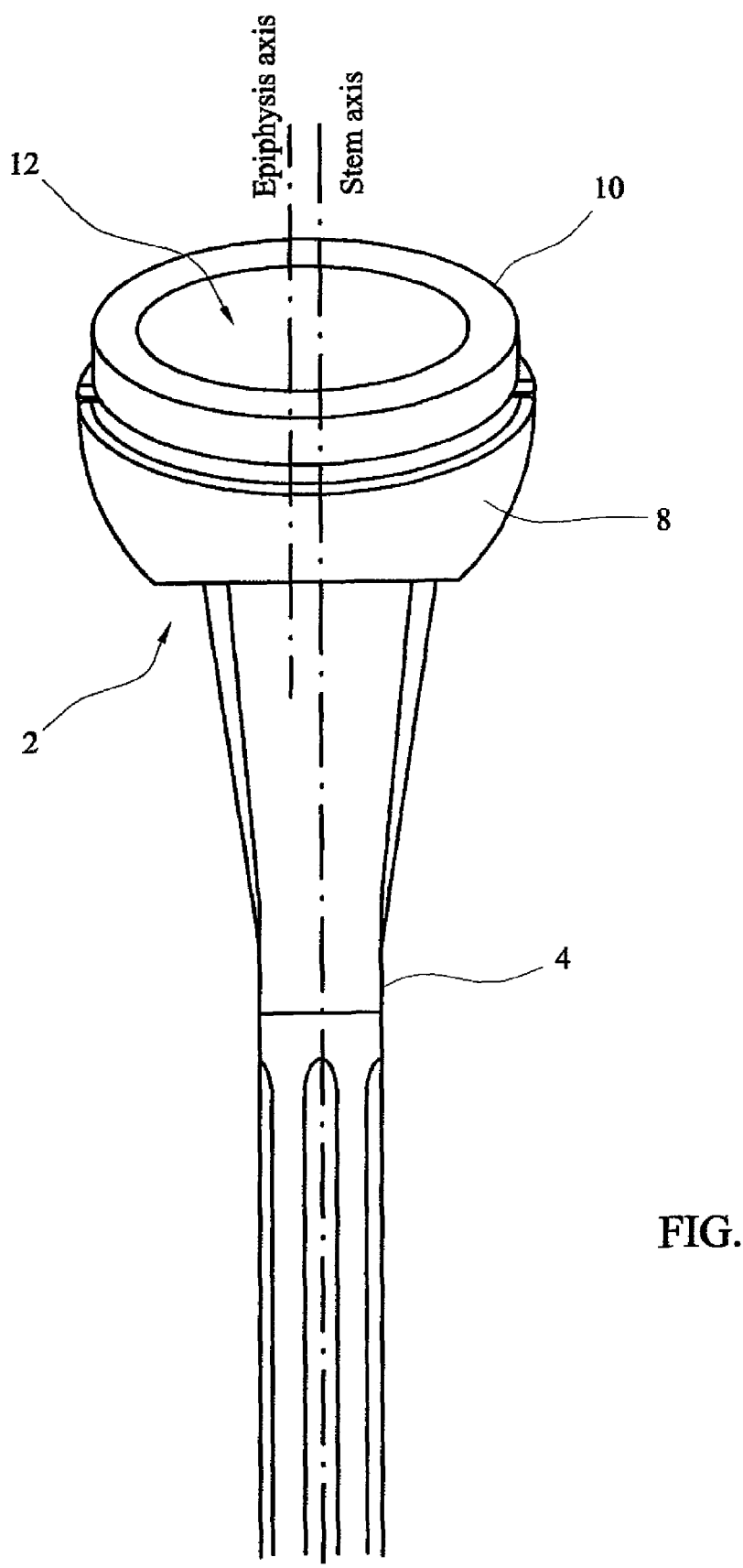
FIG. 1 is a side elevation view of a humeral component of a shoulder joint prosthesis according to the invention.
Figure 2:
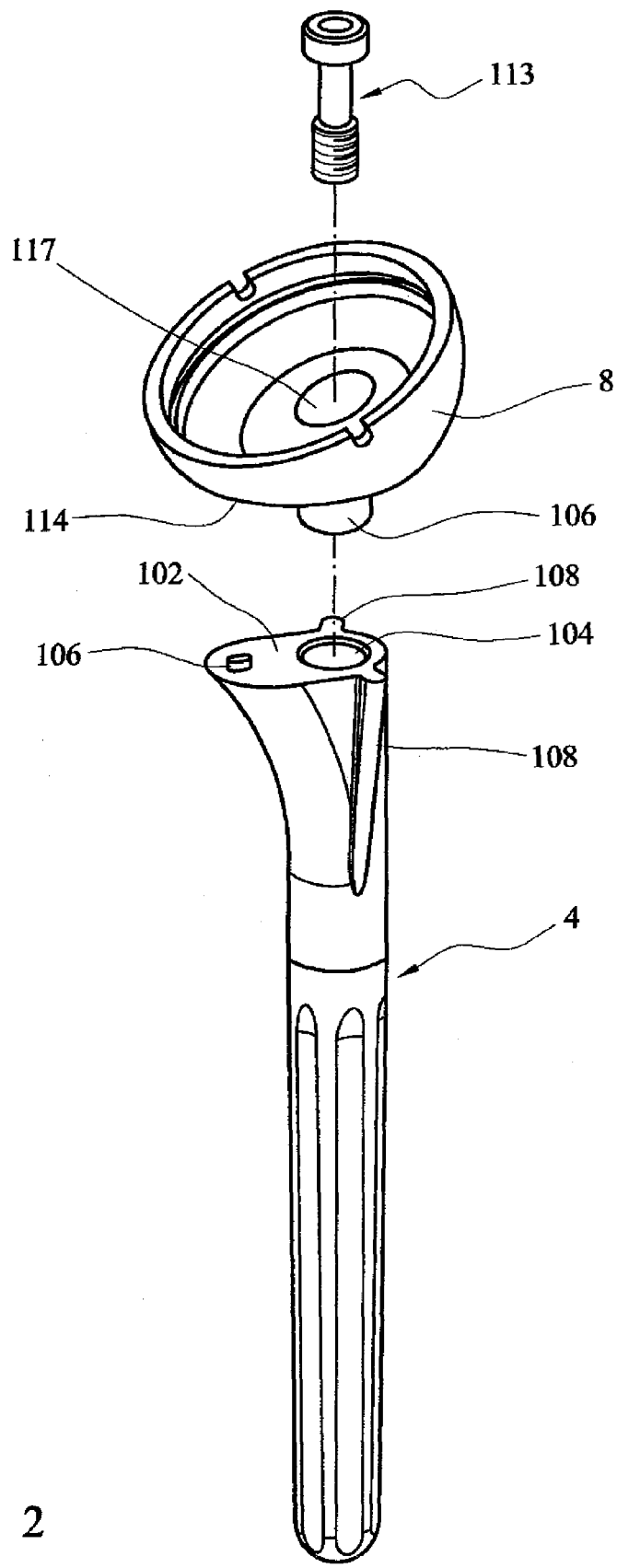
FIG. 2 is an exploded isometric view of the stem and epiphyseal parts of a humeral component according to the invention.
Figure 3:
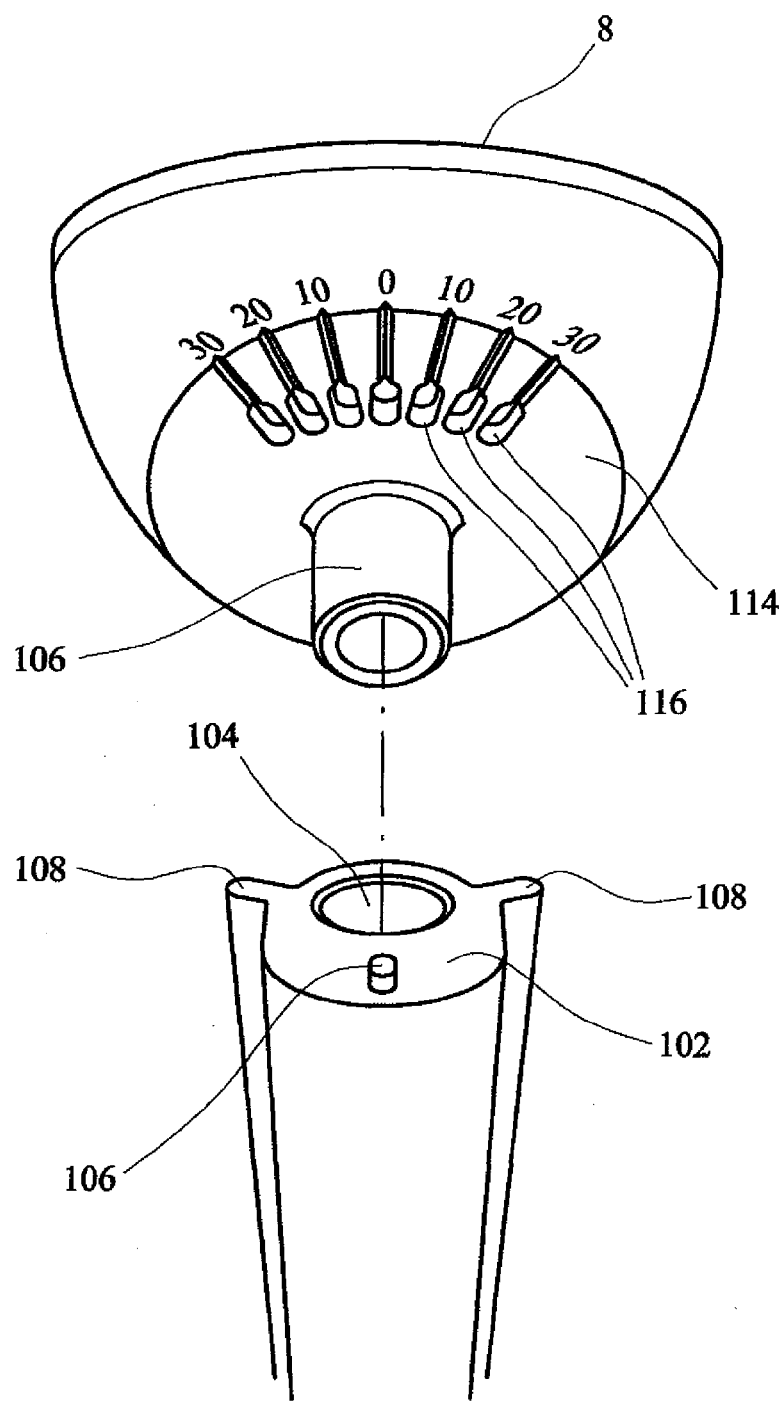
FIG. 3 is another isometric view of the stem and epiphyseal parts of a humeral component shown in FIG. 2.

Referring to the drawings, FIGS. 1 to 6 show a humeral component 2 of a reverse shoulder prosthesis. It comprises an elongate stem part 4 for location within the intramedullary cavity of the humerus 6. An epiphyseal part 8 defines a recess for a bearing part 10. The bearing part has a concave bearing surface 12 for articulation with the convex bearing surface of a glenoid component (not shown).

The stem part 4, the epiphyseal part 8 and the bearing part 10 are provided as separate modular parts which are assembled to form the humeral component prior to implantation. Features which are incorporated into modular orthopaedic joint prostheses, especially shoulder joint prostheses, which are suitable for use in the prosthesis of the present invention are known, for example from the DELTA and GLOBAL prostheses which are manufactured and sold by DePuy Products Inc, and from the AEQUALIS prosthesis which is manufactured and sold by Tornier S A. Details of one embodiment of humeral component are shown in FIGS. 2 to 5.

In the embodiment of the humeral component shown in FIGS. 2 to 5, the stem part 4 has a planar proximal face 102, with an axial bore 104 formed in it, extending normal to the proximal face and generally along the axis of the part. An upstanding lug 106 is provided on the proximal face. The stem part has two shoulders 108 at its proximal end which are to provide rotational stability of the stem part in the humerus after implantation.

The axial bore 104 is formed in two parts, with a proximal large diameter plain bore portion 110 and a distal smaller diameter threaded bore portion 112 which is configured for threaded engagement with a fixation screw 113 for the epiphyseal part 8.

The epiphyseal part 8 has a planar distal face 114 with a short spigot 116 extending from it, normal to the plane of the distal face 114. The spigot has a bore 117 extending through it which is configured so that the shank of the fixation screw 113 can extend through it. The distal face 114 of the epiphyseal part 8 has seven blind recesses 116 formed in it, in which the lug 106 on the proximal face of the humeral part can be received.

The lug and the series of blind recesses allow the angular orientation of the epiphyseal part relative to the stem part to be adjusted. This is accomplished by locating the spigot on the epiphyseal part loosely in the bore on the stem part. The epiphyseal part can be turned relative to the stem part around the axis of the stem part. The lug is located in an appropriately positioned one of the recesses 116 to lock the epiphyseal part against rotation. The epiphyseal part is then locked to the stem part by means of the fixation screw 113 engaging the threads in the small diameter portion 112 of the bore in the stem part.

Figures 4, 5:
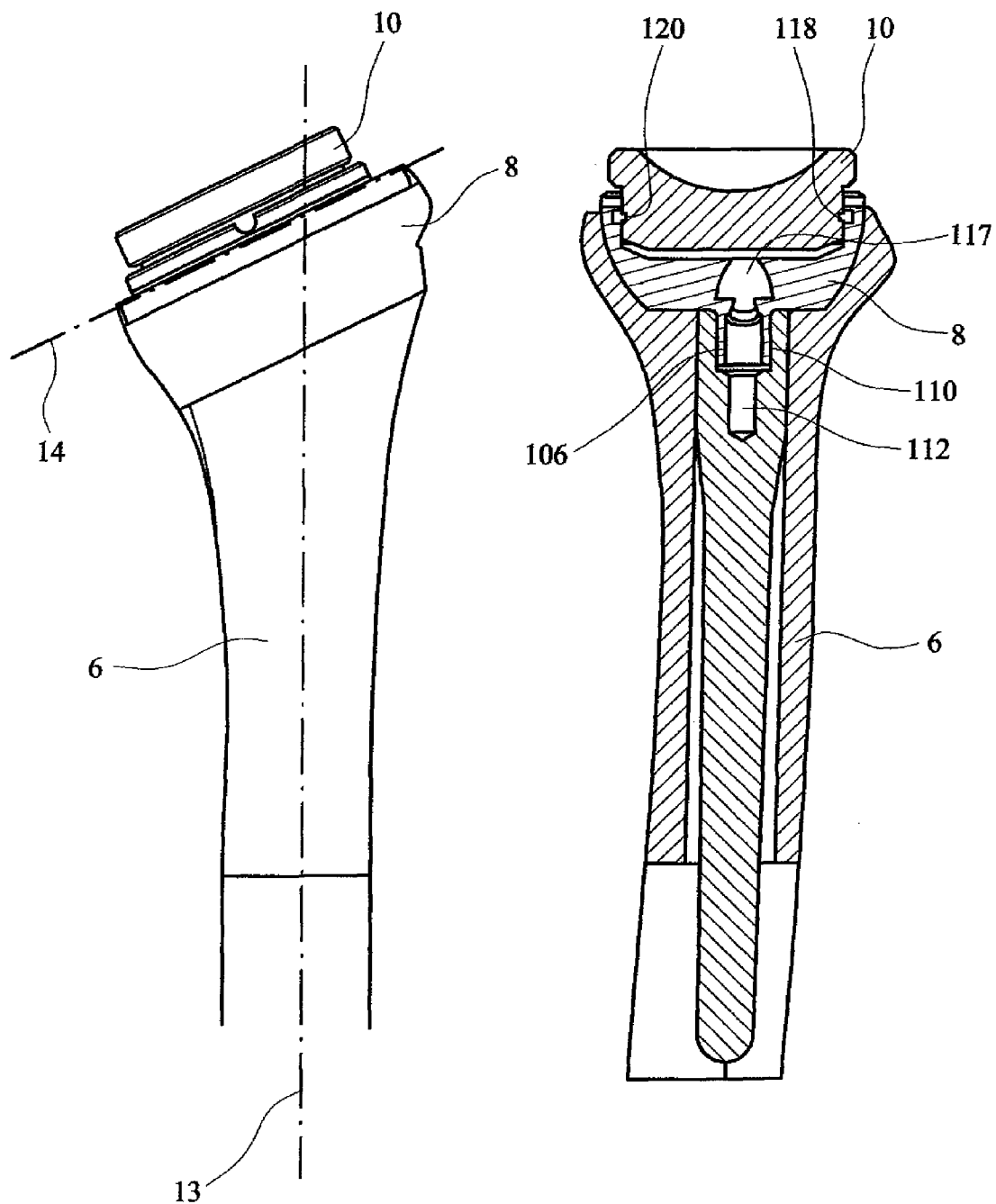
FIG. 4 is a side elevation of a humeral component according to the invention.
FIG. 5 is a sectional elevation of the humeral component shown in FIG. 4.

FIGS. 4 and 5 show in addition the bearing part 10 of the humeral component. This and the epiphyseal part have circumferential grooves 118, 120 formed in them which are aligned with one another when the parts are properly assembled. A resilient spring in the form of a zigzag wire formed into an approximately circular loop can be can be used to fasten the polymeric bearing part into the stem part of the glenoid component. The spring can be located in one of the grooves prior to assembly, which is deformed during assembly, and allowed to relax into the other of the grooves when the parts are assembled.

The use of such a spring to fasten a polymeric bearing part into the stem part of an orthopaedic joint prosthesis is well known.

The stem part 4 is formed from an alloy which is suitable for an orthopaedic joint prosthesis component such as a titanium alloy or a stainless steel. Suitable materials are known. The configuration of the stem part is as in known shoulder joint prostheses. Features of the stem part can include (a) a taper towards the distal tip, (b) axial flutes in the side walls in the portion towards the distal tip, (c) a coating over at least part of the bone engaging surface (particularly in the proximal region) of a material which promotes fixation of the implant in the intramedullary cavity, and so on. The configuration of the stem component should be optimised to ensure that it can be fixed securely in a patient's humeral cavity, as is known.

The epiphyseal part 8 of the component will generally be formed from the same material as the stem part, or at least a similar material (for example the stem part and the epiphyseal part might both be formed from metals, especially the same metal).

The bearing part of the component will frequently be formed from a polymeric material such as an ultrahigh molecular weight polyethylene (UHMWPE). Such materials are known for use in orthopaedic joint prostheses for articulation with bearing surfaces of other components provided by hard materials including metallic and ceramic materials. The bearing surface of the humeral component can be provided by materials other than polymeric materials, for example by metallic materials or ceramic materials. A bearing part need not be included in the humeral component, for example when the epiphyseal part provides the bearing surface. This can be particularly appropriate when the bearing surface of the humeral component is provided by a hard material such as a metallic material or a ceramic material.

The stem part 4 of the component defines a stem axis 13, which is intended to be aligned with the patient's humeral axis when the component is implanted.

The bearing surface of the humeral component should be shaped according to the shape of the convex bearing surface of the glenoid component with which it articulates. The bearing surface of the humeral component will generally be approximately rotationally symmetrical, for example in the form of a part of a sphere or part of an ovoid. (However, when viewed along the axis of symmetry, the bearing surface need not be circular.) The axis of symmetry of the bearing surface defines the epiphyseal axis of the humeral component.

In the humeral component of the present invention, the stem axis and the epiphyseal axis are not coincident. Preferably, they are approximately parallel. However, as shown in FIG. 1, the epiphyseal axis is offset posteriorly relative to the stem axis by about 2.5 mm.

Figure 6:
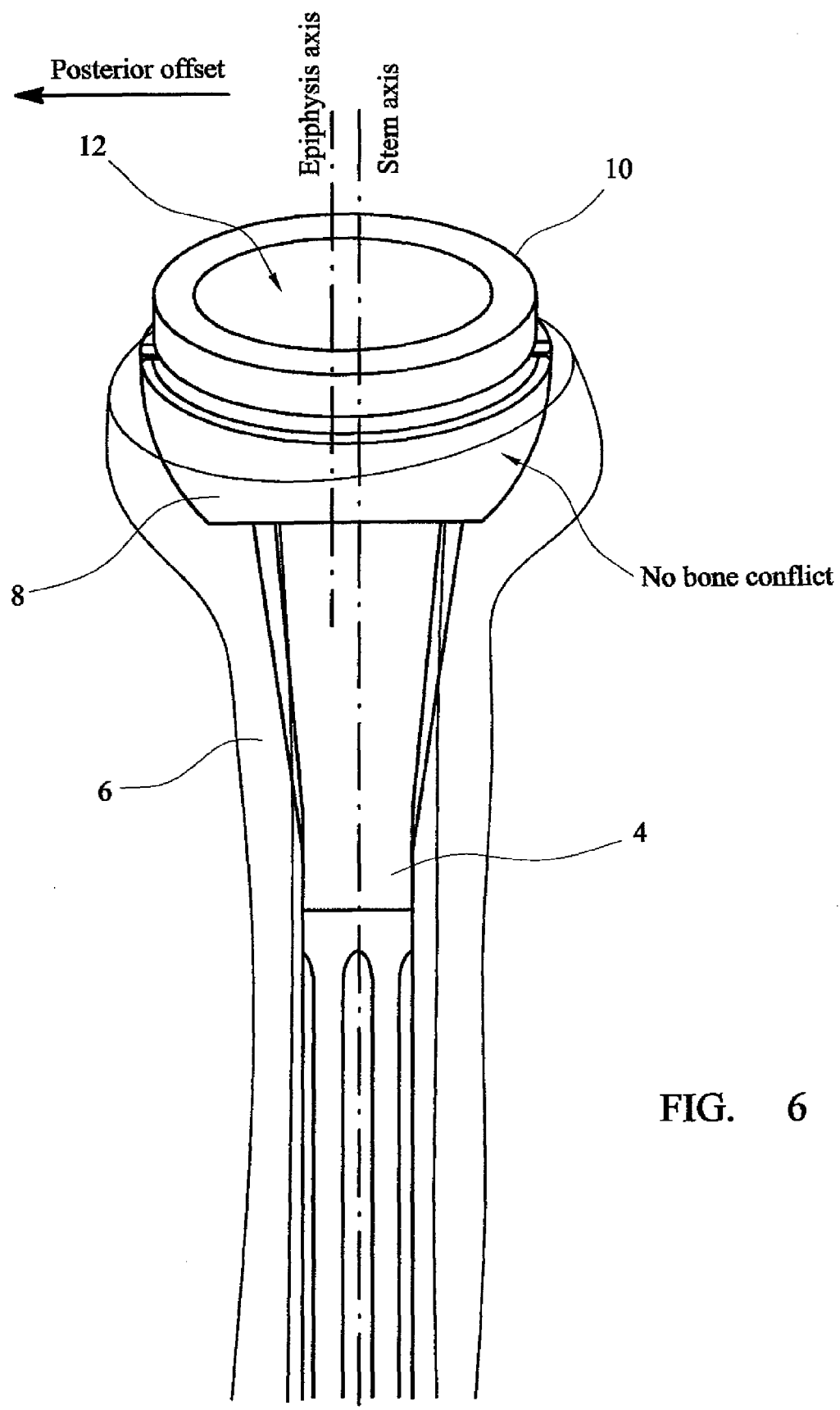
FIG. 6 is a side elevation view, partially cut away, of a humeral component according to the invention implanted in a patient's humerus.

FIG. 6 shows the humeral component described above with reference to FIG. 1 after implantation in a patient's humerus 6. As shown in FIG. 6, the humerus is prepared for implantation of the joint prosthesis by resection, as generally known. The bone is resected along a resection plane 14 which is inclined to the axis of the humerus.

It is an advantage of the present invention that the epiphyseal part 8 of the humeral component, when implanted in the humerus, can be arranged to lie wholly within the cortical tissue of the humerus on the resection plane 14. This is possible without having to compromise the size of the humeral component (which is an advantage in order to maintain optimum load transfer area on the articulating surfaces of the prosthesis). The ability to implant the humeral component without disrupting the cortical tissue of the humerus has the advantage of minimising weaknesses introduced to the bone tissue as a result of implantation of the humeral component.

Figure 7:
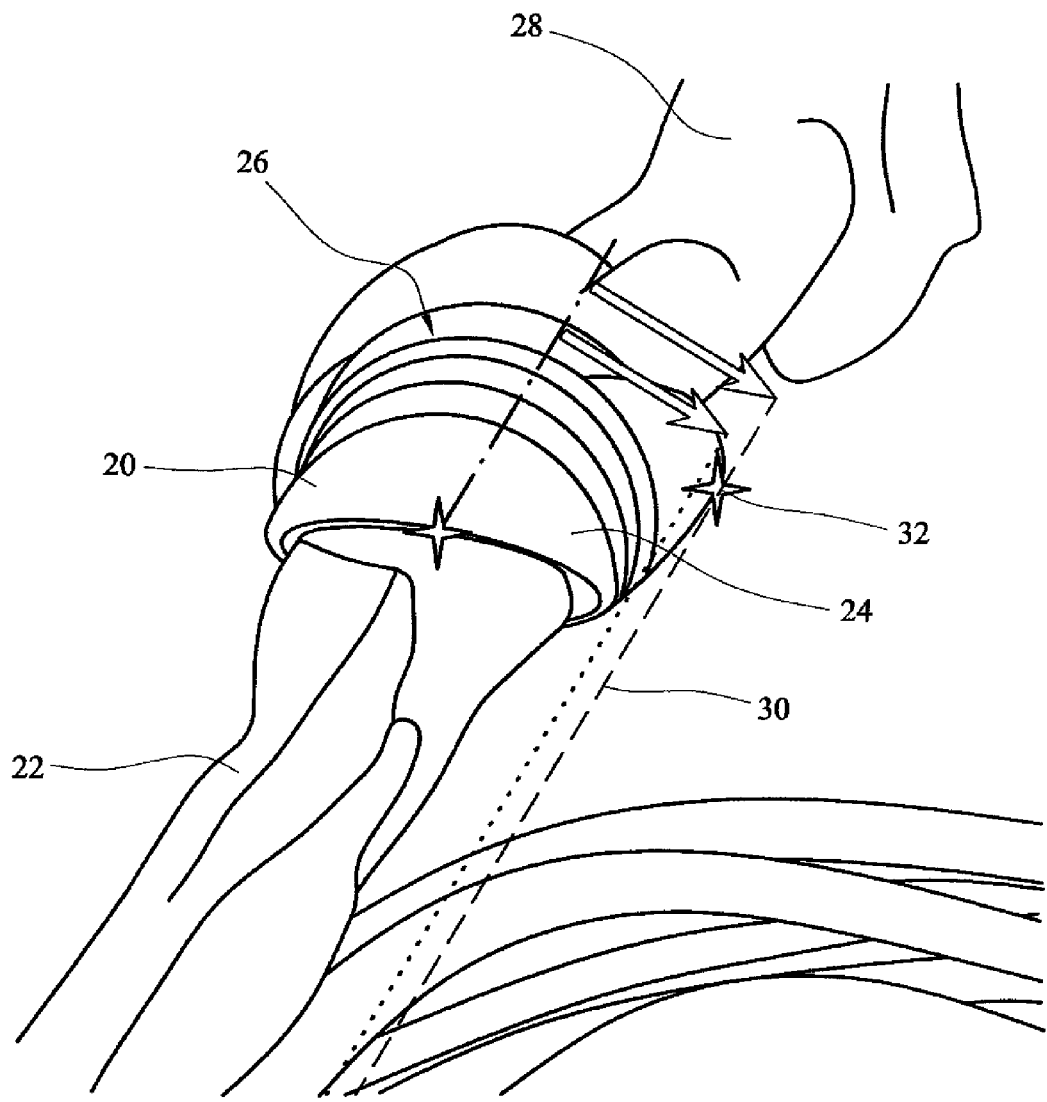
FIG. 7 is a view generally along the medial lateral axis of a shoulder joint, showing the scapula and the humerus, after implantation of a shoulder joint prosthesis according to the invention.

FIG. 7 shows a shoulder joint, with a shoulder joint prosthesis according to the invention implanted therein. A glenoid component 20 is implanted in the scapula 22, the glenoid component having a convex articulating surface 24. The glenoid component can have the features of the corresponding component of the DELTA shoulder joint prosthesis which is manufactured and sold by DePuy Products Inc. A humeral component 26, having the features of the humeral component described above with reference to FIG. 1, is implanted in the humerus 28.

Control over international rotation of the shoulder joint is provided in part by the subscapularis tendon (shown schematically by a dotted line 30). The tendon is attached to the greater tuberosity 32 on the humerus, located anteriorly relative to the humeral axis.

The mechanical advantage associated with the action of the subscapularis muscle on the shoulder joint depends on the distance between the point of attachment of the subscapularis tendon to the humerus and the centre of rotation of the joint. It is an advantage of the humeral component of the present invention that the mechanical advantage is increased as a result of the posterior offset of the centre of rotation of the joint relative to the axis of the humerus.

The invention claimed is:

1. A reverse shoulder joint prosthesis for implantation at least partially within an intramedullary cavity of a humerus bone, comprising:
    a stem part having an elongated portion configured for location within the intramedullary cavity, a stem connection feature having a connection axis, and a stem axis defined as extending centrally through the elongated portion;
    an epiphyseal part connected to the stem part and having a bone engaging surface, a concave bearing surface defining an epiphyseal axis and a epiphyseal connection feature configured to mate with the stem connection feature; and
    wherein the epiphyseal axis is offset posteriorly relative to the stem axis and the connection axis is parallel with the stem axis when the stem part is assembled with the epiphyseal part and wherein, when in use, the bone engaging surface of the epiphyseal part and at least a portion of the stem part are adapted to contact at least an aspect of the humerus bone.

2. The reverse shoulder joint prosthesis of claim 1, wherein the stem axis and the epiphyseal axis define a distance separating one from the other of at least about 1.5 mm.

3. The reverse shoulder joint prosthesis of claim 1, wherein the stem axis and the epiphyseal axis define a distance separating one from the other of not more than about 7 mm.

4. The reverse shoulder joint prosthesis of claim 1, wherein the connection axis is coincident with the stem axis when the stem part is assembled with the epiphyseal part.

5. The reverse shoulder joint prosthesis of claim 4, wherein one of the stem connection feature and the epiphyseal connection feature is a socket and the other of the stem connection feature and the epiphyseal connection feature is a spigot configured to be received in the socket.

6. The reverse shoulder joint prosthesis of claim 4, wherein the connection feature on the epiphyseal part is offset relative to the epiphyseal axis.

7. The reverse shoulder joint prosthesis of claim 1, wherein the epiphyseal part comprises a shell part that defines a recess, and a bearing part configured to be received in the shell part, the bearing part including the concave bearing surface for articulation with a glenoid component.

8. The reverse shoulder joint prosthesis of claim 7, wherein a rim of the shell part is approximately circular.

9. The reverse shoulder joint prosthesis of claim 8, wherein the rim of the shell part is approximately planar.

10. The reverse shoulder joint prosthesis of claim 9, wherein the plane defined by the rim of the shell part is approximately perpendicular to the epiphyseal axis.

11. The reverse shoulder joint prosthesis of claim 1, wherein an angle defined by the stem axis and the epiphyseal axis, when viewed along the anterior-posterior axis, is at least about 20°.

12. The reverse shoulder joint prosthesis of claim 11, wherein the angle defined by the stem axis and the epiphyseal axis, when viewed along the anterior-posterior axis, is not more than about 35°.

13. The reverse shoulder joint prosthesis of claim 1, further comprising
a glenoid component that includes a convex head part configured to be received in the epiphyseal part and articulate with the concave bearing surface.

14. The reverse shoulder joint prosthesis of claim 1, wherein the stem part and the epiphyseal part are rotatable with respect to one another about the stem axis from a first position to a second position that is angularly offset from the first position.

15. A reverse shoulder joint prosthesis for implantation at least partially within an intramedullary cavity of a humerus bone, comprising:
a stem part having an elongated portion configured for location within the intramedullary cavity, a stem connection feature having a connection axis, and a stem axis defined as extending centrally through the elongated portion;
an epiphyseal part connected to the stem part and having a bone engaging surface, a concave bearing surface defining an epiphyseal axis; and
wherein the stem part and the epiphyseal part are rotatable with respect to one another about the stem axis from a first position to a second position that is angularly offset from the first position, wherein an angle defined by the stem axis and the epiphyseal axis, when viewed along the anterior-posterior axis, is the same when the stem part and the epiphyseal part are in the first position and the second position, wherein the epiphyseal axis is offset posteriorly relative to the stem axis and the connection axis is parallel with the stem axis when the stem part is assembled with the epiphyseal part, and wherein, when in use, the bone engaging surface of the epiphyseal part and at least a portion of the stem part are adapted to contact at least an aspect of the humerus bone.

16. The reverse shoulder joint prosthesis of claim 15, wherein the angle defined by the stem axis and the epiphyseal axis, when viewed along the anterior-posterior axis, is at least about 20°.

17. The reverse shoulder joint prosthesis of claim 15, wherein the angle defined by the stem axis and the epiphyseal axis, when viewed along the anterior-posterior axis, is not more than about 35°.

18. The reverse shoulder joint prosthesis of claim 15, further comprising a glenoid component that includes a convex head part configured to be received in the epiphyseal part and articulate with the concave bearing surface.

19. The reverse shoulder joint prosthesis of claim 15, wherein the connection axis is coincident with the stem axis when the stem part is assembled with the epiphyseal part.

20. The reverse shoulder joint prosthesis of claim 19, wherein the epiphyseal part includes an epiphyseal connection feature configured to mate with the stem connection feature, and wherein one of the stem connection feature and the epiphyseal connection feature is a socket and the other of the stem connection feature and the epiphyseal connection feature is a spigot configured to be received in the socket.

21. The reverse shoulder joint prosthesis of claim 19, wherein the connection feature on the epiphyseal part is offset relative to the epiphyseal axis.

22. The reverse shoulder joint prosthesis of claim 19, wherein the stem axis and the epiphyseal axis define a distance separating one from the other of not more than about 7 mm.

23. The reverse shoulder joint prosthesis of claim 15, wherein the epiphyseal part comprises a shell part that defines a recess, and a bearing part configured to be received in the shell part, the bearing part including the concave bearing surface for articulation with a glenoid component.

24. The reverse shoulder joint prosthesis of claim 23, wherein a rim of the shell part is approximately circular.

25. The reverse shoulder joint prosthesis of claim 24, wherein the rim of the shell part is approximately planar.

26. The reverse shoulder joint prosthesis of claim 25, wherein the plane defined by the rim of the shell part is approximately perpendicular to the epiphyseal axis.

27. The reverse shoulder joint prosthesis of claim 15, wherein the stem axis and the epiphyseal axis define a distance separating one from the other of at least about 1.5 mm.

28. A reverse shoulder joint prosthesis for implantation at least partially within an intramedullary cavity of a humerus bone, comprising:
a stem part having an elongated portion configured for location within the intramedullary cavity, a stem connection feature having a connection axis, a stem axis defined as extending centrally through the elongated portion, and a proximal face having an aspect that is planar and perpendicular to the stem axis;
an epiphyseal part connected to the stem part and having a bone engaging surface, a distal face having an aspect that is planar, a concave bearing surface defining an epiphyseal axis, and an epiphyseal connection feature configured to mate with the stem connection feature; and wherein, when the stem part is assembled with the epiphyseal part, the proximal face of the stem contacts the distal face of the epiphysis, the epiphyseal axis is offset posteriorly relative to the stem axis, and the connection axis is coincident with the stem axis, and wherein, when in use, the bone engaging surface of the epiphyseal part and at least a portion of the stem part are adapted to contact at least an aspect of the humerus bone.

29. The reverse shoulder joint prosthesis of claim 28, wherein the stem part and the epiphyseal part are rotatable with respect to one another about the stem axis from a first position to a second position that is angularly offset from the first position, and wherein the angle defined by the stem axis and the epiphyseal axis, when viewed along the anterior-posterior axis, is the same when the stem part and the epiphyseal part are in the first position and the second position.

30. The reverse shoulder joint prosthesis of claim 28, wherein the stem axis and the epiphyseal axis define a distance separating one from the other of at least about 1.5 mm.

31. The reverse shoulder joint prosthesis of claim 28, wherein the stem axis and the epiphyseal axis define a distance separating one from the other of not more than about 7 mm.

32. The reverse shoulder joint prosthesis of claim 28, wherein one of the stem connection feature and the epiphyseal connection feature is a socket and the other of the stem connection feature and the epiphyseal connection feature is a spigot configured to be received in the socket.

33. The reverse shoulder joint prosthesis of claim 28, wherein the connection feature on the epiphyseal part is offset relative to the epiphyseal axis.

34. The reverse shoulder joint prosthesis of claim 28, wherein the epiphyseal part comprises a shell part that defines a recess, and a bearing part configured to be received in the shell part, the bearing part including the concave bearing surface for articulation with a glenoid component.

35. The reverse shoulder joint prosthesis of claim 34, wherein a rim of the shell part is approximately circular.

36. The reverse shoulder joint prosthesis of claim 35, wherein the rim of the shell part is approximately planar.

37. The reverse shoulder joint prosthesis of claim 36, wherein the plane defined by the rim of the shell part is approximately perpendicular to the epiphyseal axis.

38. The reverse shoulder joint prosthesis of claim 34, further comprising a glenoid component that includes a convex head part configured to be received in the epiphyseal part and articulate with the concave bearing surface.

39. The reverse shoulder joint prosthesis of claim 28, wherein an angle defined by the stem axis and the epiphyseal axis, when viewed along the anterior-posterior axis, is at least about 20°.

40. The reverse shoulder joint prosthesis of claim 28, wherein the angle defined by the stem axis and the epiphyseal axis, when viewed along the anterior-posterior axis, is not more than about 35°.

* * * * *